US009402904B2

(12) United States Patent
Imran et al.

(10) Patent No.: US 9,402,904 B2
(45) Date of Patent: *Aug. 2, 2016

(54) METHOD FOR TRANSDERMAL IONTOPHORETIC DELIVERY OF CHELATED AGENTS

(71) Applicant: Fe3 Medical, Inc., San Jose, CA (US)

(72) Inventors: Mir Imran, Los Altos Hills, CA (US); Mir Hashim, Fremont, CA (US); Sanjay Patel, Palo Alto, CA (US); Ronald J. Berenson, Mercer Island, WA (US)

(73) Assignee: Fe3 Medical, Inc., San Jose, CA (US)

( * ) Notice: Subject to any disclaimer, the term of this patent is extended or adjusted under 35 U.S.C. 154(b) by 119 days.

This patent is subject to a terminal disclaimer.

(21) Appl. No.: 14/474,027

(22) Filed: Aug. 29, 2014

(65) Prior Publication Data

US 2015/0045721 A1    Feb. 12, 2015

Related U.S. Application Data

(63) Continuation of application No. 12/459,862, filed on Jul. 7, 2009, now Pat. No. 8,821,945.

(60) Provisional application No. 61/214,642, filed on Apr. 25, 2009.

(51) Int. Cl.
| | |
|---|---|
| *A01N 59/16* | (2006.01) |
| *A01N 59/26* | (2006.01) |
| *A61N 1/30* | (2006.01) |
| *A61K 41/00* | (2006.01) |
| *A61K 9/00* | (2006.01) |
| *A61K 33/26* | (2006.01) |
| *A61K 33/42* | (2006.01) |
| *A61N 1/04* | (2006.01) |
| *A61N 1/32* | (2006.01) |
| *A61K 9/70* | (2006.01) |

(52) U.S. Cl.
CPC ........... *A61K 41/0047* (2013.01); *A61K 9/0009* (2013.01); *A61K 9/7084* (2013.01); *A61K 33/26* (2013.01); *A61K 33/42* (2013.01); *A61K 41/00* (2013.01); *A61N 1/0496* (2013.01); *A61N 1/30* (2013.01); *A61N 1/325* (2013.01); *A61K 9/703* (2013.01)

(58) Field of Classification Search
USPC ...................................... 424/646, 604; 604/20
See application file for complete search history.

(56) References Cited

U.S. PATENT DOCUMENTS

| | | | |
|---|---|---|---|
| 2,820,740 A | 1/1958 | London | |
| 3,491,187 A | 1/1970 | Ely | |
| 3,964,482 A | 6/1976 | Gerstel et al. | |
| 4,325,367 A | 4/1982 | Tapper | |
| 4,731,049 A | 3/1988 | Parsi | |
| 4,734,090 A | 3/1988 | Sibalis | |
| 4,863,897 A | 9/1989 | Dede et al. | |
| 4,886,489 A | 12/1989 | Jacobsen et al. | |
| 5,310,404 A | 5/1994 | Gyory et al. | |
| 5,328,453 A | 7/1994 | Sibalis | |
| 5,385,543 A | 1/1995 | Haak et al. | |
| 5,494,678 A | 2/1996 | Paradissis et al. | |
| 5,503,632 A | 4/1996 | Haak | |
| 5,543,098 A | 8/1996 | Myers | |
| 5,605,536 A | 2/1997 | Sibalis | |
| 5,634,899 A | 6/1997 | Shapland et al. | |
| 5,693,024 A | 12/1997 | Flower | |
| 5,797,867 A | 8/1998 | Guerrera et al. | |
| 5,928,185 A | 7/1999 | Muller et al. | |
| 5,983,130 A | 11/1999 | Phipps et al. | |
| 6,019,877 A | 2/2000 | Dupelle et al. | |
| 6,064,908 A | 5/2000 | Muller et al. | |
| 6,230,051 B1 | 5/2001 | Cormier et al. | |
| 6,256,533 B1 | 7/2001 | Yuzhakov et al. | |
| 6,314,317 B1 | 11/2001 | Willis | |
| 6,330,471 B1 | 12/2001 | Higo et al. | |
| 6,379,324 B1 | 4/2002 | Gartstein et al. | |
| 6,402,997 B1 | 6/2002 | Kwak et al. | |
| 6,512,950 B2 | 1/2003 | Li et al. | |
| 6,553,255 B1 | 4/2003 | Miller et al. | |

(Continued)

FOREIGN PATENT DOCUMENTS

| | | | |
|---|---|---|---|
| EP | 0090425 A1 | 10/1983 | |
| WO | WO 98/20869 A2 | 5/1998 | |

(Continued)

OTHER PUBLICATIONS

EPO Supplementary European Search Report and European Search Opinion for application EP09770570.1 (patent EP2320885) mailed Jun. 18, 2012.

(Continued)

*Primary Examiner* — Dennis J Parad
(74) *Attorney, Agent, or Firm* — Alston & Bird LLP

(57) ABSTRACT

Embodiments provide devices, systems and methods for the transdermal delivery of chelated compounds. One embodiment provides a method for the iontophoretic transdermal delivery of a chelated iron complex for the treatment of anemia. A first patch comprising an active electrode and a chelated iron complex is applied to the skin; a second patch containing an electrode is also applied. An electrical current is then delivered to the skin from the active electrode. The chelated complex is transported across the skin via electromotive force from the current, with the iron being substantially chromogenically unreactive with the skin during transport so that there is little or no tattooing of the skin due to the formation of insoluble oxidative products. The complex is then dissociated by phagocytosis or related process to release the iron where it may be bound by transferrin or ferritin and carried to other sites for storage or metabolic use.

38 Claims, 13 Drawing Sheets

(56) References Cited

U.S. PATENT DOCUMENTS

| | | |
|---|---|---|
| 6,584,349 B1 | 6/2003 | Sage et al. |
| 6,689,275 B1 | 2/2004 | Gupta |
| 6,692,456 B1 | 2/2004 | Eppstein et al. |
| 6,731,965 B2 | 5/2004 | Menon et al. |
| 6,779,468 B1 | 8/2004 | Gupta |
| 7,137,975 B2 | 11/2006 | Miller et al. |
| 7,141,034 B2 | 11/2006 | Eppstein et al. |
| 7,255,881 B2 | 8/2007 | Gillis et al. |
| 7,340,297 B2 | 3/2008 | Tamarkin et al. |
| 7,375,139 B2 | 5/2008 | Aldred |
| 7,437,189 B2 | 10/2008 | Matsumura et al. |
| 7,496,401 B2 | 2/2009 | Bernabei |
| 7,522,954 B2 | 4/2009 | Tedoldi |
| 7,548,778 B2 | 6/2009 | Roy |
| 7,558,625 B2 | 7/2009 | Levin et al. |
| 7,590,444 B2 | 9/2009 | Tanioka |
| 7,593,770 B2 | 9/2009 | Lerner |
| 7,611,481 B2 | 11/2009 | Cleary et al. |
| 7,816,404 B2 | 10/2010 | McCall, Jr. |
| 8,190,252 B2 | 5/2012 | Imran |
| 8,821,945 B2 | 9/2014 | Imran et al. |
| 8,996,104 B2 | 3/2015 | Berenson |
| 2002/0099356 A1 | 7/2002 | Unger et al. |
| 2003/0060798 A1 | 3/2003 | Fischer et al. |
| 2003/0065285 A1 | 4/2003 | Higuchi |
| 2003/0199808 A1 | 10/2003 | Henley et al. |
| 2003/0232084 A1 | 12/2003 | Groman et al. |
| 2004/0138646 A1 | 7/2004 | Walla |
| 2005/0020487 A1 | 1/2005 | Klaus et al. |
| 2005/0042270 A1 | 2/2005 | Aldred |
| 2005/0085751 A1 | 4/2005 | Daskal et al. |
| 2005/0131337 A1 | 6/2005 | Phipps et al. |
| 2005/0148996 A1 | 7/2005 | Sun et al. |
| 2005/0165393 A1 | 7/2005 | Eppstein |
| 2005/0209565 A1 | 9/2005 | Yuzhakov |
| 2005/0213286 A1 | 9/2005 | Michel et al. |
| 2005/0238704 A1 | 10/2005 | Zumbrunn et al. |
| 2005/0273046 A1 | 12/2005 | Kwiatkowski et al. |
| 2006/0025715 A1 | 2/2006 | Henley et al. |
| 2006/0134227 A1 | 6/2006 | Bortz et al. |
| 2006/0216339 A1 | 9/2006 | Ambron et al. |
| 2006/0217654 A1 | 9/2006 | Matsumura et al. |
| 2006/0229549 A1 | 10/2006 | Hause et al. |
| 2006/0258973 A1 | 11/2006 | Volt |
| 2007/0012622 A1 | 1/2007 | Wash |
| 2007/0065521 A1 | 3/2007 | Venkataraman et al. |
| 2007/0066934 A1 | 3/2007 | Etheredge et al. |
| 2007/0083185 A1 | 4/2007 | Carter |
| 2007/0083186 A1 | 4/2007 | Carter et al. |
| 2007/0161600 A1 | 7/2007 | Helenek et al. |
| 2007/0224253 A1 | 9/2007 | Franklin |
| 2007/0270732 A1 | 11/2007 | Levin et al. |
| 2008/0027369 A1 | 1/2008 | Carter et al. |
| 2008/0058699 A1 | 3/2008 | Hause et al. |
| 2008/0058700 A1 | 3/2008 | Hause et al. |
| 2008/0081051 A1 | 4/2008 | Sabin et al. |
| 2008/0086072 A1 | 4/2008 | Bonutti et al. |
| 2008/0114282 A1 | 5/2008 | Carter |
| 2008/0154178 A1 | 6/2008 | Carter et al. |
| 2008/0287497 A1 | 11/2008 | Anderson et al. |
| 2009/0036821 A1 | 2/2009 | Lai |
| 2009/0062720 A1 | 3/2009 | Anderson et al. |
| 2009/0124572 A1 | 5/2009 | Nelson |
| 2009/0163597 A1 | 6/2009 | Goto et al. |
| 2009/0171313 A1 | 7/2009 | Yamamoto et al. |
| 2009/0221985 A1 | 9/2009 | Bukshpan et al. |
| 2009/0254018 A1 | 10/2009 | Nakayama |
| 2009/0259176 A1 | 10/2009 | Yairi |
| 2009/0281475 A1 | 11/2009 | Nisato et al. |
| 2009/0299264 A1 | 12/2009 | Matsumura et al. |
| 2009/0299267 A1 | 12/2009 | Durand |
| 2010/0130910 A1 | 5/2010 | Berenson |
| 2010/0130912 A1 | 5/2010 | Berenson |
| 2010/0331759 A1 | 12/2010 | Imran |
| 2010/0331810 A1 | 12/2010 | Imran |
| 2010/0331811 A1 | 12/2010 | Imran |
| 2011/0082411 A1 | 4/2011 | Imran |
| 2015/0258035 A1 | 9/2015 | Berenson |

FOREIGN PATENT DOCUMENTS

| | | |
|---|---|---|
| WO | WO 01/00204 A1 | 1/2001 |
| WO | WO 2007/098058 A2 | 8/2007 |
| WO | WO 2009/158032 A1 | 12/2009 |
| WO | WO 2010/123584 A2 | 10/2010 |

OTHER PUBLICATIONS

EPO Supplementary European Search Report and European Search Opinion for application EP10767443.4 (patent EP2421601) mailed Nov. 6, 2012.

Murthy et al., "Irontophoresis™: Transdermal Delivery of Iron by Iontophoresis," J. Pharm. Sci., 98(8): 2670-2676 (2009).

PCT International Preliminary Report on Patentability for application PCT/US2010/023112 issued Aug. 11, 2011.

PCT International Preliminary Report on Patentability for application PCT/US2010/023744 issued Aug. 16, 2011.

PCT International Preliminary Report on Patentability for application PCT/US2010/040109 issued Jan. 4, 2012.

PCT International Preliminary Report on Patentability for application PCT/US2010/051541 mailed Apr. 19, 2012.

PCT International Search Report for application PCT/US2009/003837 mailed Nov. 16, 2009.

PCT International Search Report for application PCT/US2010/023112 mailed Sep. 27, 2010.

PCT International Search Report for application PCT/US2010/023744 mailed Sep. 27, 2010.

PCT International Search Report for application PCT/US2010/040109 mailed Feb. 25, 2011.

PCT International Search Report for application PCT/US2010/051541 mailed Jun. 24, 2011.

PCT Written Opinion of the International Searching Authority for application PCT/US2009/003837 mailed Nov. 16, 2009.

PCT Written Opinion of the International Searching Authority for application PCT/US2010/001227 mailed Dec. 23, 2010.

PCT Written Opinion of the International Searching Authority for application PCT/US2010/023112 mailed Sep. 27, 2010.

PCT Written Opinion of the International Searching Authority for application PCT/US2010/023744 mailed Sep. 27, 2010.

PCT Written Opinion of the International Searching Authority for application PCT/US2010/051541 mailed Jun. 24, 2011.

U.S. Appl. No. 12/459,183, Final Office Action mailed Nov. 13, 2013.

U.S. Appl. No. 12/459,183, Non-Final Office Action mailed Dec. 27, 2011.

U.S. Appl. No. 12/459,183, Notice of Allowance mailed Nov. 17, 2014.

U.S. Appl. No. 12/459,186, Advisory Action mailed Jan. 28, 2014.

U.S. Appl. No. 12/459,186, Final Office Action mailed Sep. 18, 2013.

U.S. Appl. No. 12/459,186, Non-Final Office Action mailed Apr. 5, 2012.

U.S. Appl. No. 12/459,186, Non-Final Office Action mailed Aug. 27, 2014.

U.S. Appl. No. 12/459,186, Non-Final Office Action mailed Aug. 31, 2011.

U.S. Appl. No. 12/459,862, Final Office Action mailed Jan. 29, 2013.

U.S. Appl. No. 12/459,862, Non-Final Office Action mailed Dec. 15, 2011.

U.S. Appl. No. 12/459,862, Requirement for Restriction/Election mailed Jul. 6, 2011.

U.S. Appl. No. 12/537,243, Final Office Action mailed Oct. 28, 2011.

U.S. Appl. No. 12/537,243, Non-Final Office Action mailed Apr. 8, 2011.

U.S. Appl. No. 12/537,243, Notice of Allowance mailed Jan. 19, 2012.

U.S. Appl. No. 12/658,637, Non-Final Office Action mailed Mar. 23, 2012.

U.S. Appl. No. 12/658,637, Notice of Allowance mailed Jul. 9, 2012.

(56) References Cited

OTHER PUBLICATIONS

U.S. Appl. No. 12/824,146, Non-Final Office Action mailed Jun. 1, 2012.
U.S. Appl. No. 12/824,147, Non-Final Office Action mailed Jun. 1, 2012.
PCT International Preliminary Report on Patentability for application PCT/US2009/003837 issued Jan. 5, 2011.
PCT International Preliminary Report on Patentability for application PCT/US2010/001227 issued Oct. 25, 2011.
U.S. Appl. No. 12/459,186, Final Office Action mailed May 12, 2015.
U.S. Appl. No. 12/459,186, Non-Final Office Action mailed Jan. 11, 2016.

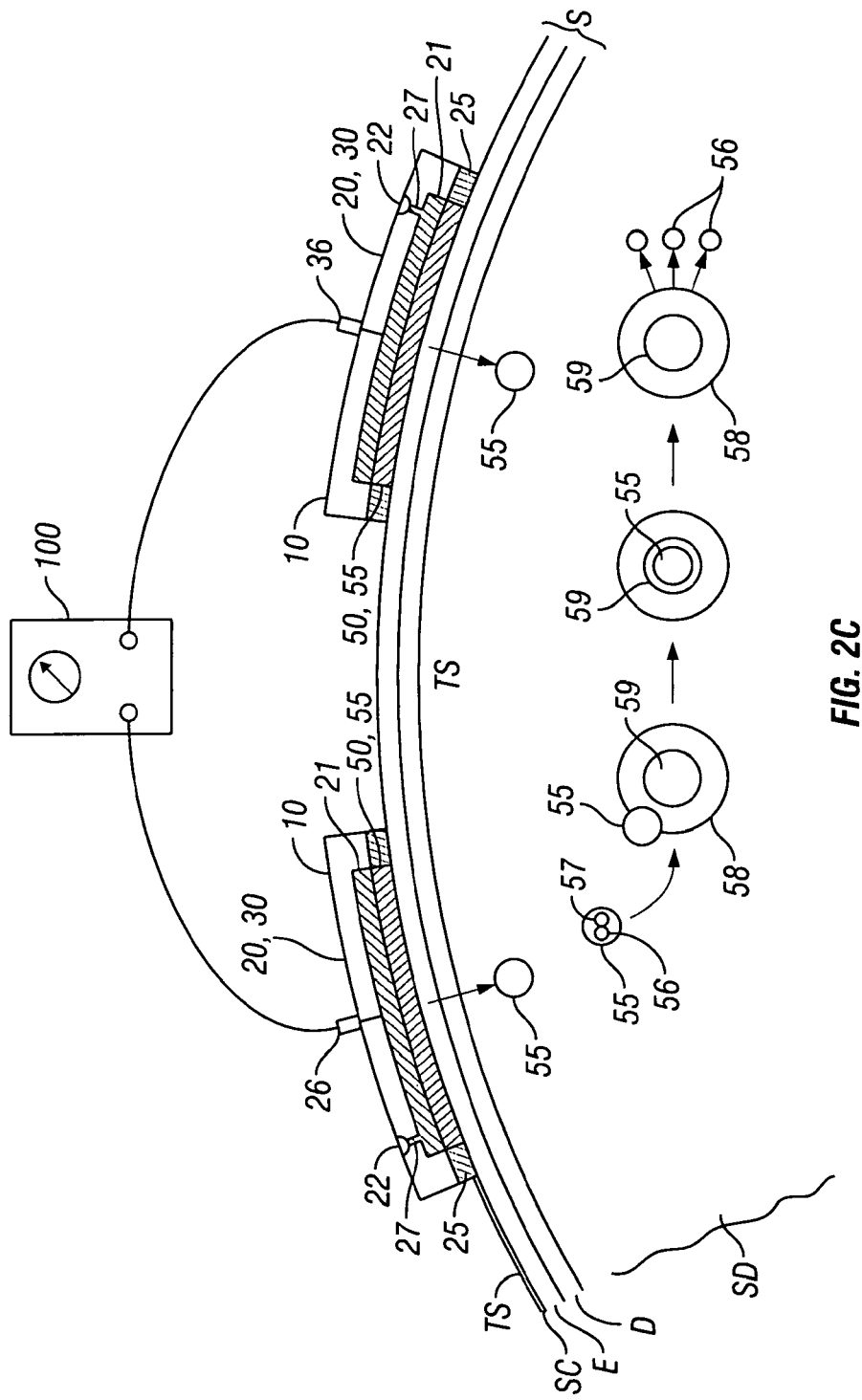

METHOD FOR TRANSDERMAL IONTOPHORETIC DELIVERY OF CHELATED AGENTS

RELATIONSHIP TO OTHER APPLICATIONS

This application claims the benefit of priority to U.S. Provisional Application Ser. No. 61/214,642 filed Apr. 25, 2009, entitled "Method for Transdermal Iontophoretic Delivery of Chelated Agents" which is fully incorporated by reference herein. This application also claims the benefit of priority to U.S. patent application Ser. No. 12/459,186, filed Jun. 25, 2009, entitled "Patches And Methods For The Transdermal Delivery Of A Therapeutically Effective Amount Of Iron", which claims the benefit of priority to U.S. Provisional Application Ser. No. 61/075,720 filed Jun. 25, 2008, entitled "Patches And Methods For The Transdermal Delivery Of A Therapeutically Effective Amount Of Iron" which are fully incorporated by reference herein. This application also claims the benefit of priority to U.S. patent application Ser. No. 12/459,183, filed Jun. 25, 2009, entitled "Patches And Methods For The Transdermal Delivery Of A Therapeutically Effective Amount Of Iron", which claims the benefit of priority to U.S. Provisional Application Ser. No. 61/075,720 filed Jun. 25, 2008, entitled "Patches And Methods For The Transdermal Delivery Of A Therapeutically Effective Amount Of Iron" which are fully incorporated by reference herein.

FIELD OF THE INVENTION

Embodiments described herein relate to transdermal delivery of various therapeutic agents. More specifically, embodiments described herein relate to transdermal iontophoretic delivery of various chelated complexes. Still more specifically, embodiments described herein relate to transdermal iontophoretic delivery of various iron chelated complexes.

BACKGROUND

Nutrient deficiency is a world wide heath problem. Iron deficiency in particular is the most common form of nutritional deficiency in the world, affecting over 3 billion people in the Third World alone. It is associated with a number of diseases and conditions and is blamed for 100,000 maternal deaths during childbirth each year as well as 134,000 deaths among children. It is also co-morbid with a number of parasitic infections and is a key underlying factor in impaired mental development in children.

Iron deficiency anemia is one of the more serious conditions caused by iron deficiency. It is an advanced stage of iron deficiency and occurs when the dietary intake or absorption of iron is insufficient, and hemoglobin, which contains iron, cannot be formed.

Children and pre-menopausal women are the two groups most prone to developing this disease. The principal cause of iron deficiency anemia in premenopausal women is blood lost during menses. Causes in children include malnutrition during pregnancy, malnutrition, premature birth, GI bleeding, and parasitic infection.

The typical form of treatment for iron deficient anemia includes oral or intravenous delivery with various ferrous compounds. However, both of these treatments have a number of limitations. Oral iron preparations in particular have many disadvantages. First and foremost, they cause gastrointestinal side effects including nausea, bloating, constipation, and diarrhea. This leads to discontinuation of iron supplementation in approximately 40-66% of the patients taking such supplements. Furthermore, the absorption of iron is variable and affected by the oral ingestion of other compounds. For example, oral ingestion of food products reduces iron absorption by approximately 50%, which is problematic since many patients take iron with food in order to reduce the gastrointestinal side effects.

Second, many drugs are known to reduce iron absorption. For example, oral ingestion of antacids and other drugs that reduce stomach pH is known to decrease iron absorption. In turn, oral ingestion of iron also reduces the absorption of many drugs, including antibiotics. Additionally, many conditions associated with iron deficiency anemia respond poorly to oral iron supplementation because iron cannot be properly absorbed through the cells of the gastrointestinal system. This is especially true of certain inflammatory conditions of the bowel, such as Crohn's disease. Additionally, diseases associated with functional iron deficiency, such as the anemia of renal failure, are also associated with limited absorption of orally administered iron. This is also true of many other so-called "inflammatory conditions" associated with functional iron deficiency, such as those associated with rheumatoid arthritis and other autoimmune diseases, as well as anemia secondary to cancer or cancer chemotherapy treatment. This is especially true in patients with these conditions who are treated with erythropoietin, who have considerably increased demands for iron.

Intravenous administration also has a number of limitations. These include pain and infection at the injection site, the requirement to be connected to an IV drip for a prolonged period of administration (to reduce the risk of anaphylaxis), and the requirement to mix, store and administer the medication in liquid form using sterile technique. The latter can be particularly problematic in third world countries where adequate refrigeration and sterile needles are not readily available, limiting shelf life and exposing the patient to infection. Also, IV administration can include several risk factors including anaphylaxis, and cardiovascular complications.

Thus, there is a need for improved methods of drug delivery for the treatment of iron deficiency including anemia and other related medical conditions which can extend shelf life and are more easily used in settings lacking refrigeration or sterile medical supplies.

BRIEF SUMMARY

Embodiments described herein provide a device, system and method for the transdermal iontophoretic delivery of drugs and other therapeutic agents. Many embodiments provide a device, system and method for the transdermal iontophoretic delivery of chelated drugs and therapeutic agents. Particular embodiments provide a device, system and method for the delivery of chelated iron compounds for the treatment of iron deficiency including the treatment of iron deficiency anemia (herein after "anemia") and related conditions. Such embodiments are particularly useful for treatment of anemia by transdermally delivering controlled doses of iron in a form well tolerated by the patient while producing minimal tattooing, marking or other chromogenic effects on the skin due to oxidative reaction of the iron with the skin.

One embodiment provides a method for the iontophoretic transdermal delivery of a chelated iron complex for the treatment of anemia comprising the following approach. A patch comprising an active electrode and a chelated iron complex is applied to the skin; a second patch containing an electrode serving as a return electrode is also applied. In many embodiments, (including those using alternating current to deliver the chelated complex), the second patch may include the chelated complex and the second electrode may thus function as an active electrode as well.

The chelated complex can comprise an iron ion (e.g., ferrous $Fe^{2+}$; or ferric $Fe^{3+}$) that is electrostatically bound to a chelating agent such as pyrophosphate. An electrical current is then delivered to the skin from the active electrode with current flow penetrating through the layers of the skin into the subdermal layers before it flows back to the return electrode. The current serves to transport the chelated complex across the skin via electromotive force, with the iron ion being substantially chromogenically unreactive with the skin during transport so that there is little or no tattooing or marking of the skin due to the formation of insoluble oxidative products created by reactive iron ions ($Fe2+$ or $Fe3+$). These reactive iron ions can form colored precipitates in the skin which result in a tattoo. The iron complex is then dissociated in subdermal tissue by phagocytosis or related intracellular processes to release the iron where it is quickly bound by transferrin. The complex may also be absorbed into the blood stream transported in its chromogenically unreactive form to the spleen where the complex is disassociated by phagocytosis or other cellular processes.

Another embodiment provides a transdermal iontophoretic delivery device comprising an active electrode assembly conformable to a contour of a skin surface, and a return electrode assembly conformable to a contour of a skin surface. In many embodiments, the electrode assemblies comprise skin conformable patches. Accordingly, in these and related embodiments the transdermal iontophoretic delivery device comprises a transdermal iontophoretic delivery patch device, herein after a "patch device". The active electrode assembly includes a reservoir for the therapeutic agent, a tissue contacting porous layer in fluidic communication with the reservoir, and a connector for coupling the active electrode assembly to an electrical power source such as a battery powered source.

In some embodiments the patch may also include a self sealing port. The self sealing port comprises a silicone or other elastomeric material and allows the electrode assembly to be filled using an external container of therapeutic agent solution such as a squeezable bottle.

The return electrode assembly comprises a tissue contacting conductive layer and a connector for coupling the electrode assembly to the electrical power source. In many embodiments the return electrode assembly can also comprise an active electrode assembly and can thus include a reservoir, a self sealing port and a porous tissue contacting layer.

In another aspect, the invention provides a kit for iontophoretic transdermal drug/therapeutic agent delivery which includes an embodiment of the iontophoretic transdermal device and a mixing container. The mixing container has a premeasured dose of therapeutic agent in solid form. Typically, the therapeutic agent will be part of a therapeutic agent composition which can include one or more pharmaceutical excipients such as preservatives. The therapeutic agent composition is configured to be stored for an extended period in solid form and dissolved in liquid to produce a therapeutic agent solution having sufficient concentration to treat a medical condition of a patient, such as anemia, using transdermal iontophoretic delivery of the therapeutic agent solution. In many embodiments, the therapeutic agent comprises a therapeutically effective amount of iron in the form of one or more chelated iron compounds including, ferric pyrophosphate, for the treatment of anemia.

The mixing container also includes an applicator having a tip for penetrating the self sealing port of the active electrode assembly, and a port for adding liquid to dissolve the therapeutic agent. This port can also comprise a self sealing port made from an elastomeric material to allow for injection of mixing fluids using a syringe or tissue penetrating end of an IV kit.

The mixing container has a shape, volume and radial elastic quality to allow a user to mix the therapeutic agent in the added liquid to prepare the therapeutic agent solution and then deliver the solution to the active electrode by inserting the applicator tip through the self sealing port of the electrode assembly and squeezing the mixing container. In various embodiments the mixing container can comprise a squeezable bottle fabricated from one or more resilient polymers such as HDPE, or polypropylene.

Further details of these and other embodiments and aspects of the invention are described more fully below, with reference to the attached drawing figures.

BRIEF DESCRIPTION OF THE DRAWINGS

FIG. 2c is a schematic side view showing delivery of a chelated therapeutic complex from a transdermal iontophoretic patch device placed on the skin.

FIG. 5a shows the entire packaging and the packaged kit including instructions for use, while FIG. 5b shows the use of flaps on the packaging for opening the packaging.

FIG. 7a shows methods for filling the mixing container by an IV bag or syringe; FIG. 7b shows the mixed therapeutic agent solution; FIG. 7c shows use of the mixing container to fill the active electrode assembly.

FIG. 10a shows the separate DC and AC components, while FIG. 10b shows them combined.

DETAILED DESCRIPTION OF THE INVENTION

Many embodiments described herein provide a system and method for transdermal iontophoretic delivery of various therapeutic agents including chelated complexes. As used herein, a chelated complex comprises a therapeutic moiety such as an iron ion that is electrostatically bound by an inactive moiety such as pyrophosphate. Also as used herein, the term transdermal delivery refers to the delivery of a compound, such as a drug or other therapeutic or biological agent, through one or more layers of the skin (e.g., epidermis, dermis, etc). The layers of the skin include the epidermis, E, dermis, D and subdermis, SD. The upper most layer of the epidermis includes the stratum corneum, SC.

Iontophoresis is a non-invasive method of propelling high concentrations of a charged substance, known as the active agent, transdermally by repulsive electromotive force using a small electrical charge. The active agent can include a drug or other therapeutic agent or biological compound. The charge is applied by an electrical power source to an active electrode assembly placed on the skin which contains a similarly charged active agent and a solvent in which it is dissolved. Current flows from the electrode assembly through the skin and then returns by means of a return or counter electrode assembly also placed on the skin. A positively charged electrode assembly, termed the anode will repel a positively charged active agent, or anion, into the skin, while a negatively charged electrode assembly, termed the cathode, will repel a negatively charged active agent, or cation, into the skin.

Figure 1:
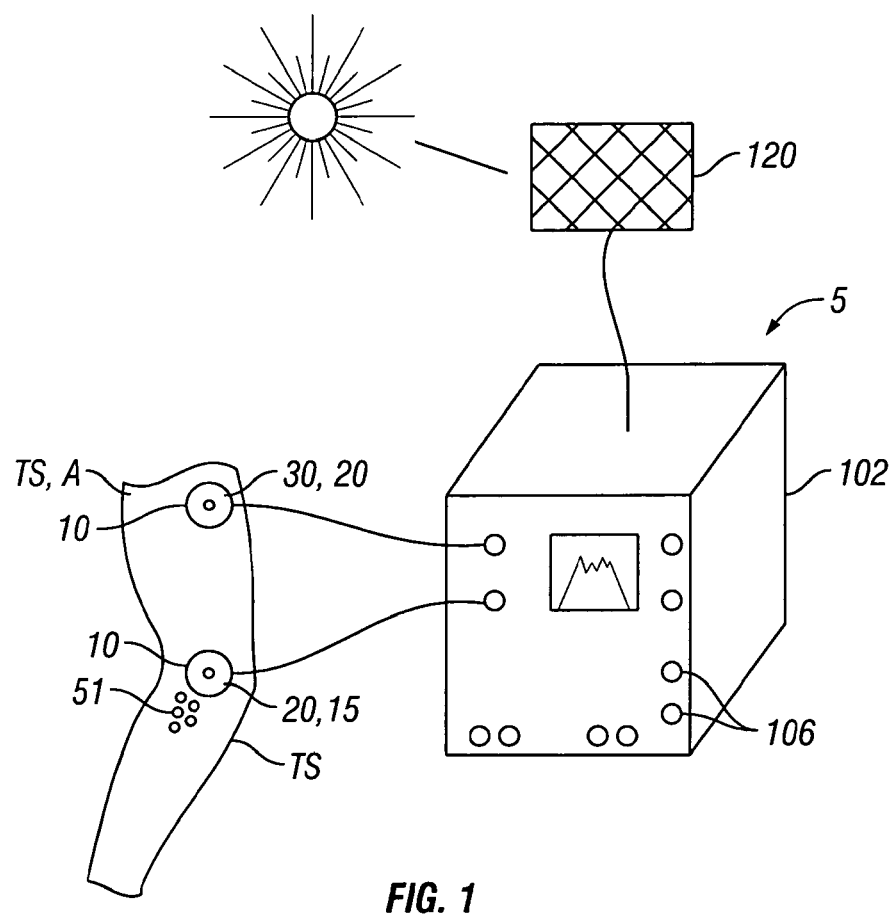
FIG. 1 is a schematic view of an embodiment of a system for the transdermal iontophoretic delivery of various therapeutic agents.

Referring now to FIGS. 1-7, one embodiment of a system 5 for the transdermal iontophoretic delivery of a therapeutic agent to a tissue site TS (such as the arm A) on the skin S of patient comprises at least two electrode assemblies 15 including an active electrode assembly 20 and a return electrode assembly 30; and a power supply 100 as is shown in the embodiment of FIG. 1. Collectively, the active and return electrodes 20 and 30 are comprise a transdermal iontophoretic delivery device 10 also described herein as patch device 10 or patch 10.

Figure 2A:
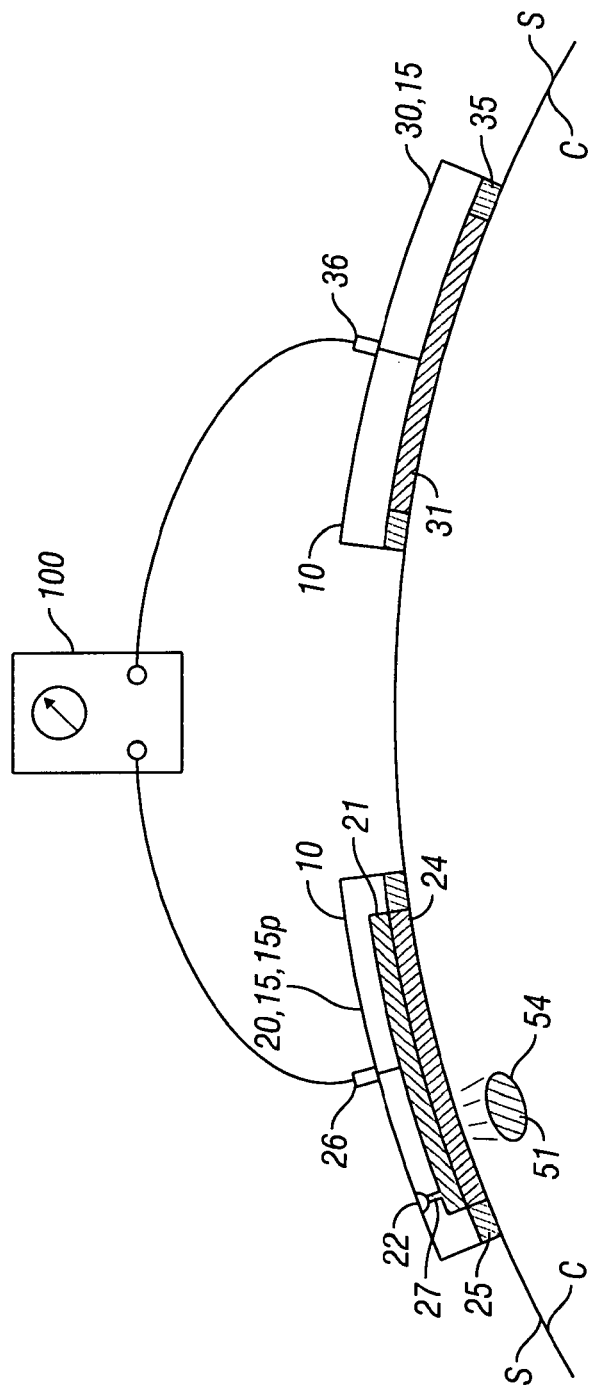
FIG. 2a is a schematic side view showing placement of an embodiment of a transdermal iontophoretic patch device on the surface of the skin, wherein the device comprises an active electrode assembly and a return electrode assembly.
Figure 2B:
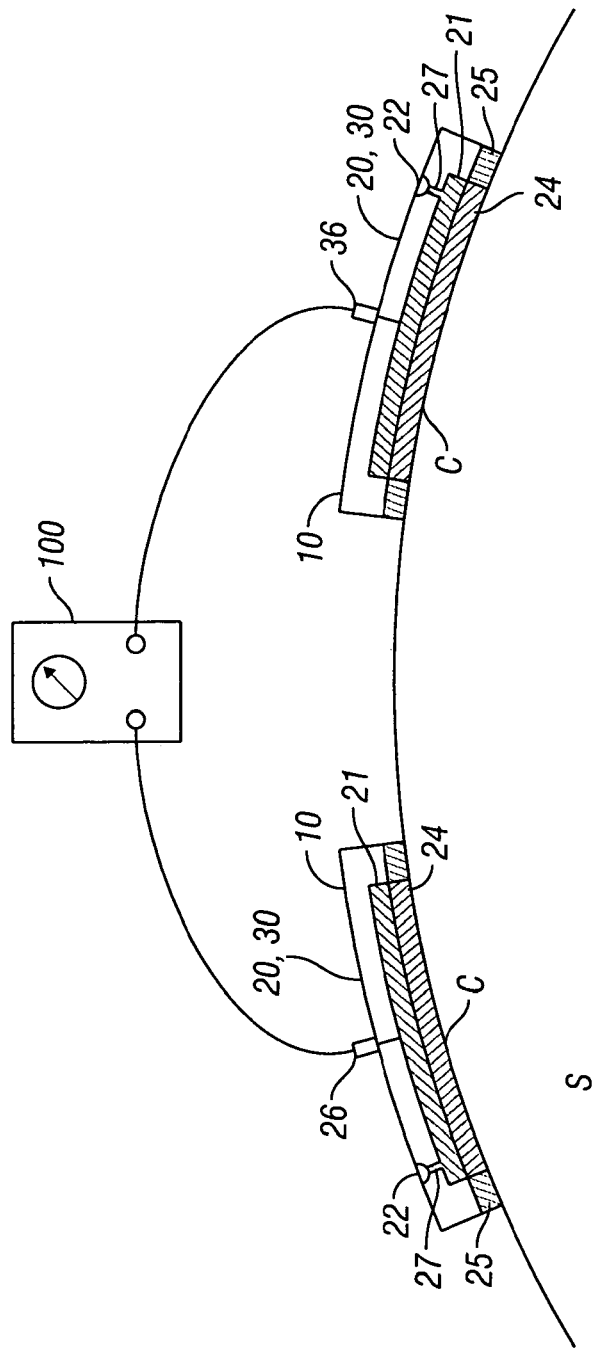
FIG. 2b is a schematic side view showing placement of an embodiment of a transdermal iontophoretic patch device on the surface of the skin, wherein the device comprises two active electrode assemblies.
Figure 3A:
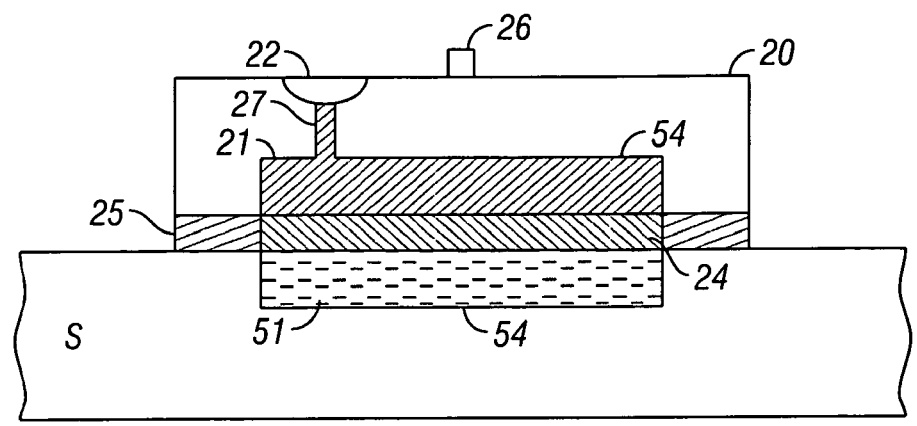
FIGS. 3a and 3b are side and top views showing an embodiment of an active electrode assembly.
Figure 3B:
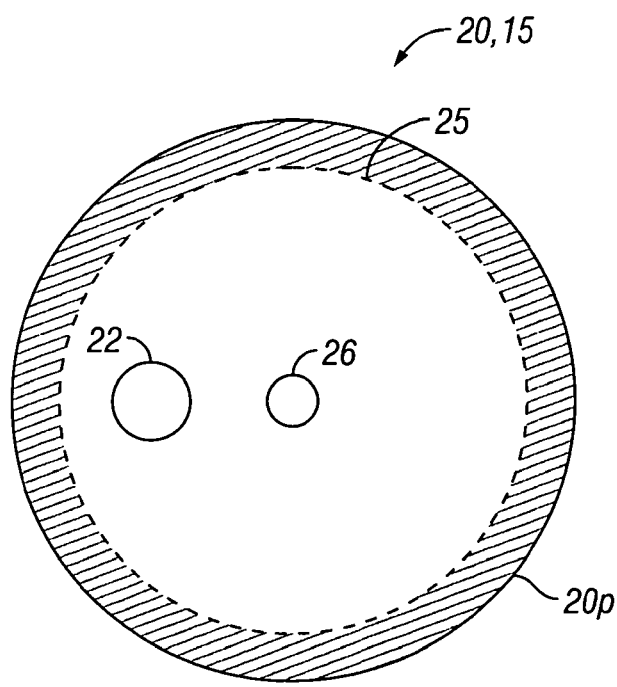

The active and return electrode assemblies are conformable to a contour C of a skin surface S as is shown in the embodiments of FIGS. 2a and 2b. In many embodiments, the electrode assemblies comprise skin conformable patches 15p fabricated from layers of elastomeric or other flexible polymer material. The active electrode 20 assembly includes a reservoir 21 for the therapeutic agent, a tissue contacting porous layer 24 in fluidic communication with the reservoir, an adhesive layer 25 for adhering the assembly to the skin and an electrical connector 26 for coupling the electrode assembly 20 to an electrical power source 100 such as a battery and/or solar powered source.

In some embodiments, the active electrode can include a self sealing port 22 fluidically coupled to the reservoir for filling the reservoir with therapeutic agent. The self sealing port 22 comprises a silicone or other elastomeric material and allows the electrode assembly to be filled with therapeutic solution 54 using a mixing container 40 described herein and/or a syringe and to do so using sterile technique. In some embodiments the port can include a channel 27 fluidically coupling the port 22 to the reservoir 21. The porous conductive layer 24 can comprise polymer fibers such as PET fibers or a polymer foam known in the art. The porosity of the porous conductive layer 24 can be selected depending upon the particular therapeutic agent, and current voltage regimen. High porosities can be selected for higher molecular weight therapeutic agents and/or therapeutic agent solutions 54 having greater viscosity. The adhesive layer 25 will typically be positioned on the perimeter 25p of the electrode assembly and comprise various releasable adhesives known in the biomedical electrode arts.

The return electrode assembly 30 comprises a tissue contacting conductive layer 31, an adhesive layer 35 and a connector 36 for coupling the electrode assembly to the electrical power source. In many embodiments, the return electrode assembly 30 can also comprise an active electrode assembly 20 as is shown in the embodiment of FIG. 2b and can thus include a reservoir 21, a self sealing port 22, channel 27 and a porous tissue contacting layer 24.

Figure 4:
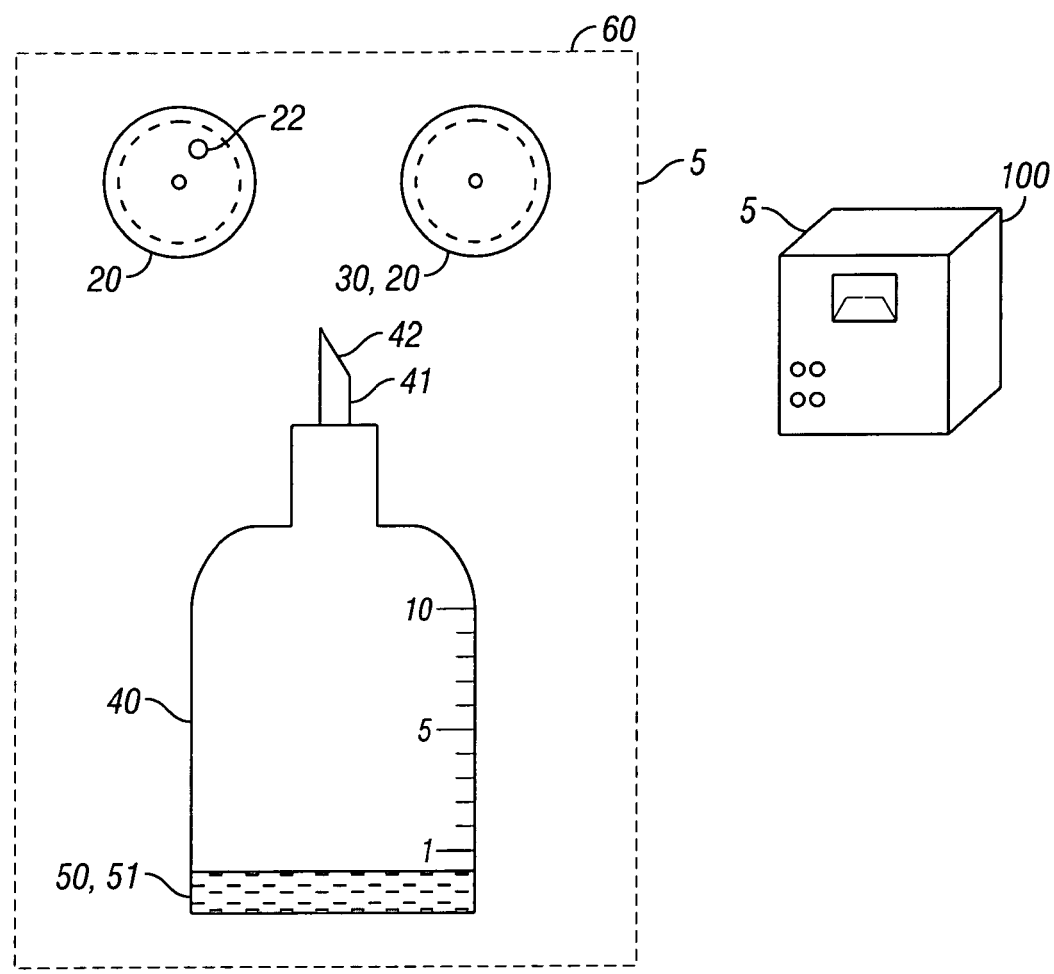
FIG. 4 is a schematic side view showing an embodiment of a kit and system for the transdermal iontophoretic delivery of a therapeutic agent.
Figure 5B:
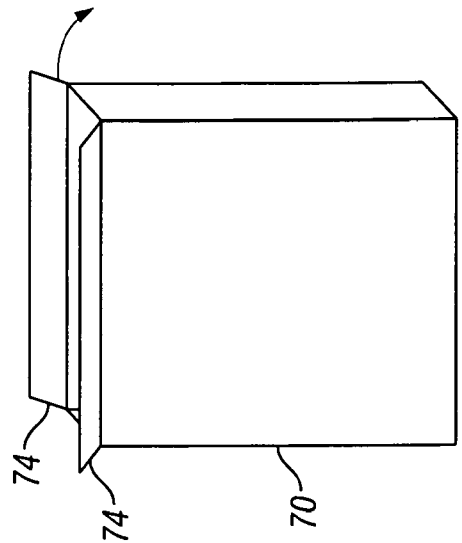
FIGS. 5a and 5b are perspective views showing embodiments of packaging for the transdermal iontophoretic delivery kit.
Figure 5A:
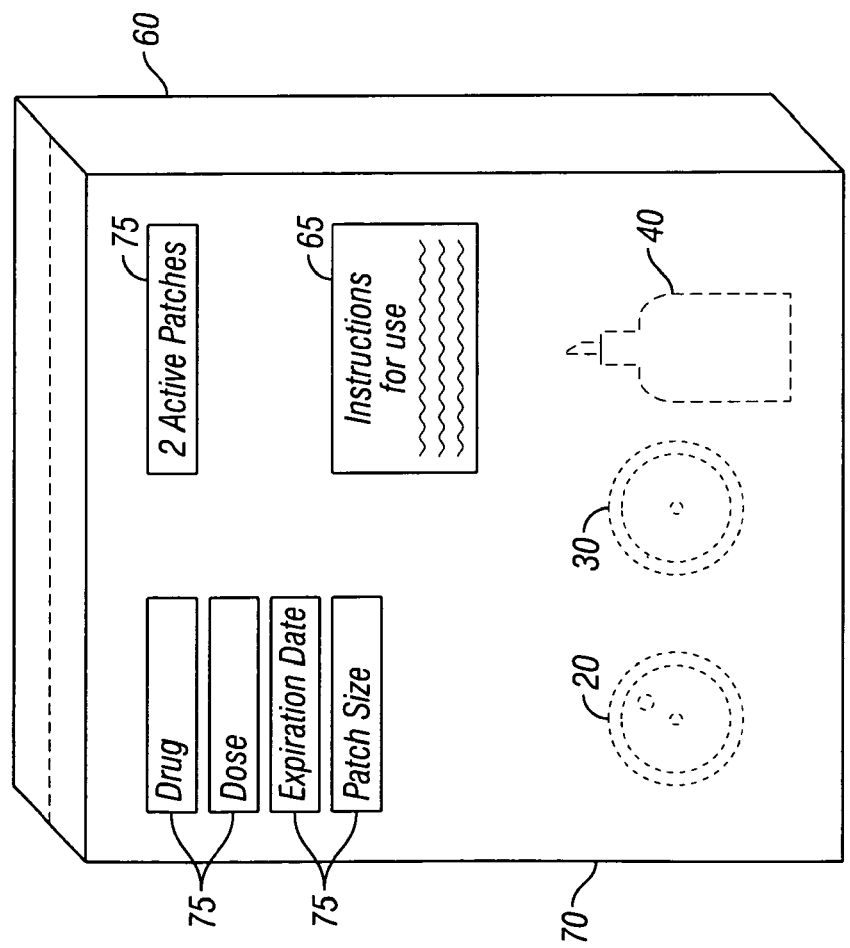

In various embodiments, the electrode assemblies 20 and 30 together with a mixing container 40, which includes solid form therapeutic agent 51 can comprise a kit 60 for the transdermal iontophoretic delivery of a therapeutic agent 51, as is shown in the embodiment of FIG. 4. In various embodiments, system 5 can include kit 60 and power supply 100 as is also shown in FIG. 4. Kit 60 can be packaged in sterile packaging 70 as shown in the embodiments of FIGS. 5a and 5b. In these embodiments, kit 60 can also include instructions for use 65 of the kit detailing the specific therapeutic agent dose, mixing instructions and power/current delivery regimen to be used. Packaging 70 can include various identifying indicia 75 such as indicia identifying the type, dose and expiration date of agent 51 as well as the patch size of electrodes 20 and 30. The packaging can also be constructed from vapor impermeable/resistant materials to so as to protect kit 60 from oxidation and water vapor and thus extend the shelf life of kit 60 including therapeutic agent 51. Additionally the packaging 70 can include peelable flaps 74 to facilitate opening of the packaging using sterile technique.

Figure 6:
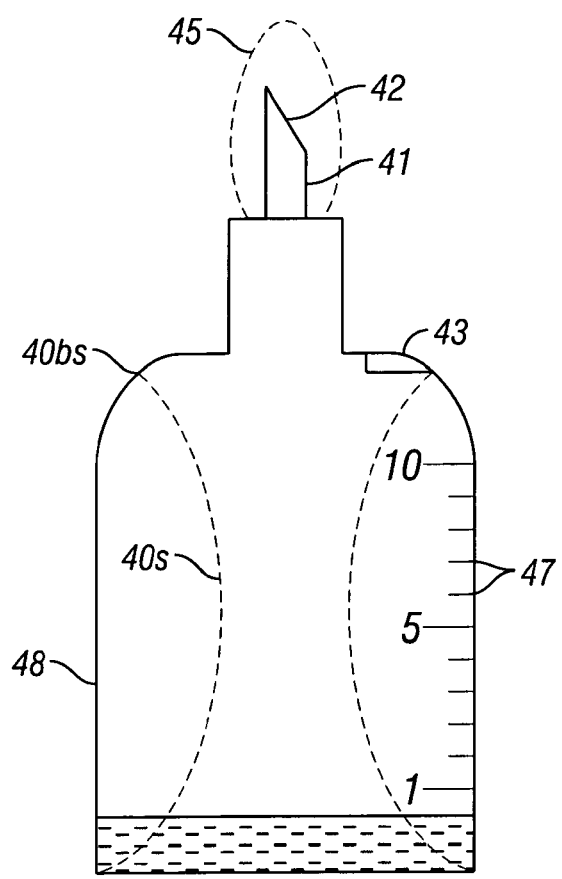
FIG. 6 is a side view illustrating an embodiment of a mixing container having a premeasured dose of therapeutic agent.

The mixing container 40 has a premeasured dose of therapeutic agent 51 in solid form as is shown in the embodiment of FIG. 6. Typically the therapeutic agent will be part of a therapeutic agent composition 50 which can include one or more pharmaceutical 52 excipients such as preservatives. The therapeutic agent composition 50 is configured to be stored for an extended period in solid form and dissolved in liquid to produce a therapeutic agent solution 54 having sufficient concentration to treat a medical condition of a patient such as anemia using transdermal iontophoretic delivery of the therapeutic agent solution 54.

Figure 7C:
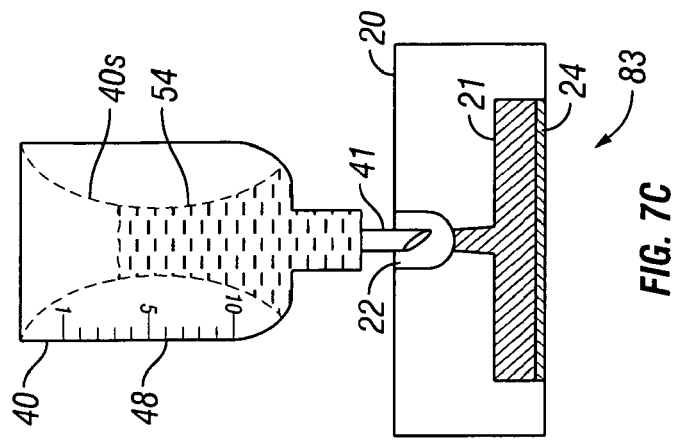
FIGS. 7a-7c are schematic side views illustrating use of the mixing container.
Figure 7B:
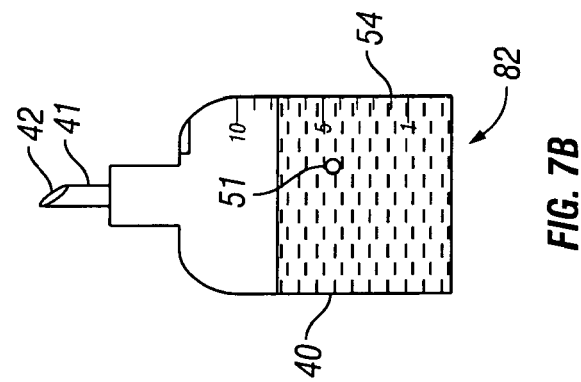
Figure 7A:
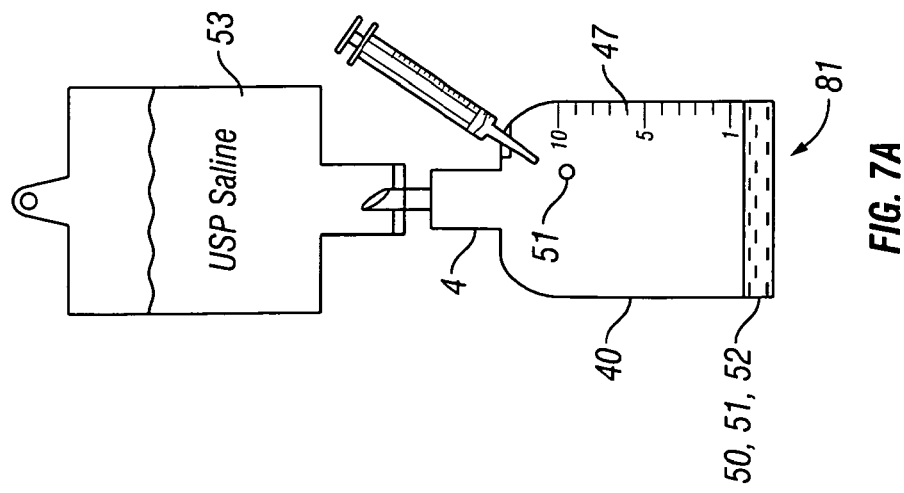

Referring now to FIGS. 6, 7a, 7b and 7c, the mixing container 40 includes an applicator 41 having a tip 42 for penetrating the self sealing port 22 of the active electrode assembly, and a port 43 for adding liquid 53 such as saline or distilled water to dissolve the therapeutic agent composition so as to form therapeutic agent solution 54. Applicator 41 can also include a removable sheath 46. Port 43 can also comprise a self sealing port made from an elastomeric material to allow for injection of mixing fluids using a syringe or tissue penetrating end of an IV bag as is shown in the embodiment of FIG. 7a. The mixing container can also include various measurement indicia 47 to assist in filling the container with a selected amount of liquid 53.

The mixing container 40 has a shape, volume and radial elastic quality to allow a user to mix the therapeutic agent 51 in the added liquid 53 to prepare the therapeutic agent solution 54 and then deliver the solution to the active electrode assembly 20 by inserting the applicator tip 42 through the self sealing port 22 of the electrode assembly and squeezing the mixing container 40 into a squeezed state 40s as is shown in the embodiments of FIGS. 7a-7c. Accordingly, the mixing container 40 comprises a squeezable bottle 40s fabricated from one or more resilient polymers, such as HDPE or polypropylene. Also, applicator 41 and tip 42 have sufficient column strength and sharpness to be able to puncture port 22 by holding the body of the container 48 and jabbing the port 22.

In an embodiment of a method for using kit 60 and container 40, after the user opens packaging 70, he fills container 40 in filling step 81 by either inserting the tip 42 into a sterile IV bag of liquid 53 or through use of a syringe as is shown in FIG. 7a. Then he shakes the container in a mixing step 82 to mix the therapeutic composition 50 to form therapeutic solution 54 as is shown in FIG. 7b. Finally, he adds the mixed solution 54 to the electrode assembly 20 by inserting tip 42 through sealable port 22 and squeezing the container in an electrode assembly filling step 83 as is shown in FIG. 7c.

As discussed herein, in many embodiments, therapeutic agent 51 is part of a therapeutic composition 50 that comprises the solidly formed therapeutic agent 51 and one or more pharmaceutical excipients 52. Suitable excipients 52 can include preservatives and buffers to maintain a selected pH of the solution 54. One or more of these excipients 52 along with therapeutic agent 51 can be solidified using methods such as crystallization and lyophilization. In various embodiments, therapeutic agent composition 50 and agent 51 can also be in a concentrated liquid form that is diluted in mixing container 40. Whether in solid or liquid form, therapeutic agent composition and agent 50 and 51 are diluted using a solvent 53 also known as carrier 53 to form a therapeutic agent solution 54 that is loaded into the active electrode assemblies 20 using mixing container 40 or by other means. Suitable solvents 53 can comprise distilled water and various aqueous solutions including saline or buffered saline.

In various embodiments, the therapeutic agent 51 can include without limitation: iron compounds, antibiotics (e.g., penicillin, ampicillin, erythromycin, ciprofloxacin, vancomycin, etc.), antibodies, proteins, polypeptides, insulin and other glucose regulating compounds, various anti-diarrheal drugs (e.g., Loperamide oxide) various chemotherapeutic agents (e.g., doxorubicin), various vaccines (e.g., diphtheria, cholera, tetanus, flu, measles and polio vaccines; vaccines can also include be in the form of deactivated pathogens as well as antibodies), and various hormones having birth control properties (e.g., estrogen and progesterone as well as combinations thereof). The therapeutic agents can also include various pro-drugs which are metabolized into their active form once released into the body. Suitable pro-drugs can include antiviral nucleoside analogs, lipid-lowering statins, antibody-directed/gene-directed enzyme prodrugs for chemotherapy, etoposide phosphate, valganciclovir and fosamprenavir. Again, these therapeutic agents can be lyophilized, including vaccines, antibodies, proteins and peptides.

In specific embodiments, the therapeutic agent 51 and agent composition 50 can comprise one or more ferrous salts for the treatment of anemia such as ferric chloride or ferrous chloride; other salts are also contemplated. The composition can also comprise one or more preservatives such as ascorbic acid to preserve the charge/ionic state of the ferrous salt (having a +2 charge state) to prevent it from converting to a ferric salt (having a +3 charge state). For embodiments using ferrous chloride, the therapeutic solution 54 can be mixed to have a concentration in the range from 200 to 1000 mg/ml with specific embodiments of 300, 400, 500 and 750 mg/ml.

The amount or dose of the respective therapeutic agent 51 and/or therapeutic composition 50 to be included in the mixing container 40 can be determined based on the condition to be treated (e.g., anemia, diabetes, etc.) and patient weight, age, etc. Also, dosages can be based on known therapeutically effective doses for a particular condition that are delivered orally, intravenously or by other delivery means (e.g., intranasally, inhalation, etc.) with adjustment for different absorption/uptake of the known method (e.g., in the case of orally delivered iron compounds). For example, in the case of orally delivered iron compounds (e.g., ferrous sulfate) for the treatment of anemia, typically 50 mg of elemental iron are delivered, of which only 10 to 25 mg are actually absorbed into the blood stream. Accordingly, the dose of elemental iron in the mixing container can be in the range of 10 to 25 mg or 10 to 50 mg with specific embodiments of 10, 15, 20, 25, 30, 40 and 50 mg. Additionally, in particular embodiments, dose response curves can be developed for the transdermal iontophoretic delivery of particular therapeutic agents using known pharmacological methods. These methods can include measurement of various biomarkers of iron status in the body including one or both of serum iron concentrations as well as % transferrin iron saturation (herein transferrin iron saturation). Again, adjustment can be made for the weight and age of the patient as well as their particular condition, e.g., gestational anemia.

In particular embodiments, the dose of a chelated iron complex 55 in the mixing container 40 and/or patch 10 can be adjusted or titrated based on measurement of one or more biomarkers of iron status such as serum iron concentration or transferrin iron saturation. Other such biomarkers can include serum/plasma concentrations of one or more of ferritin, transferrin, C-reactive protein, hemoglobin (e.g., hematocrit) and bilirubin. One or both of the rate of delivery of chelated iron complex 55 into the skin can also be titrated based on measurement of one or more biomarkers of iron status. Such titration of delivery rates can be achieved by adjustment of the electrical delivery parameters discussed herein, e.g., current, voltage, waveform, delivery time, etc. In particular embodiments, titration of delivery rates of the therapeutic complex can be achieved by modulation of the current used for iontophoretic delivery. The modulation can be in frequency, amplitude or both.

In certain embodiments, therapeutic composition 50 can comprise a chelated complex 55 which comprises a therapeutic agent or moiety 56 that is electrostatically bound to a chelating agent or moiety 57. In many cases, the therapeutic moiety 56 has a positive charge such as for an iron moiety for treating anemia, and the chelating moiety has a negative charge. The chelated complex 55 can be delivered to the skin S and underlying subdermal tissue SD using various iontophoretic transdermal methods described herein. This can include applying to the skin a patch 10 containing the chelated complex dissolved in solution and then delivering a current to drive the complex into the skin and underlying tissue SD as is shown in FIG. 2c. Once transported across the skin S and into underlying sub dermal tissue SD, the therapeutic moiety 56 remains bound by the unreactive moiety 57 until acted on by one or more cellular mechanisms (e.g., phagocytosis).

The above process allows the chelated complex 55 to be chromogenically unreactive with the skin during transport across the skin. Specifically, the complex produces little or no chromogenic marking in the skin including the epidermal and subdermal layers. In the case of iron, such markings, known as tattoos, result from the formation of insoluble oxidative products (specifically, insoluble iron oxide salts) created by reactive iron ions (e.g., $Fe^{2+}$ or $Fe^{3+}$). These salts then precipitate in the epidermal or dermal layers to form colored precipitates causing the tattoo. Use of chelated iron complex minimizes or eliminates the production of these salts and thus eliminates the development of tattoos or other related discolorations causing cosmetic changes to the skin. As is discussed below, use of chelated iron complexes also reduces the amount of cosmetic change due to burning, irritation or other injury to the skin resulting from current delivery.

Suitable chelated iron complexes 55 which are chromogenically unreactive include ferric pyrophosphate, and related iron salts. In these and related embodiments, the ferric or other iron ion is sufficiently electrostatically bound by the pyrophosphate or other inactive moiety so that the ferric ion is not available to form insoluble salts within the skin. Thus the iron ion is substantially chromogencically unreactive with the skin. Other suitable chelated iron complexes can include ferrous or ferric complexes comprising edetate, ethylenediamineedetate and/or ethylenediaminesuccinate. In addition to the selection of the chelated complex 55, chromogenic marking during skin transport can be also reduced by selection of one or more of the electrical parameters (e.g., current, voltage, waveform, etc.) of iontophoretic delivery.

In the case of ferric pyrophosphate or like molecules, dissociation occurs by various cellular processes such as phagocytosis, where the chelated complex 55 is engulfed by macrophages 58 or other cells 58 and the molecule is broken down in the cell cytoplasm 59 of the macrophage 58 into its therapeutic agent components by various enzymes within the macrophage or other phagocyte. Phagocytosis can occur subdermally proximate to tissue site TS or in the spleen or other locations. For ferric pyrophosphate, the elemental iron (in the form of ferric ions) released by phagocytosis may then be bound by transferrin where it is then transferred by the plasma to be used throughout the body in various metabolic processes including synthesis of various biological compounds such as heme synthesis, and red blood cell formation in the bone marrow as well as storage in the liver where it is taken up by hepatocytes. The ferric ion may also be taken up and bound intracellularly by a ferritin molecule, which is the main intracellular iron storage protein. This can either occur directly within the macrophage or indirectly when the iron is carried and released by transferrin to a location where it is then taken and bound within the location by ferritin. For patients suffering from iron deficient anemia, the iron released by phagocytosis or other metabolic process can be used to enhance the amount of heme synthesis in the liver or the bone marrow. This in turn, can enhance the amount of hemoglobin in the blood.

In addition to reducing or eliminating the formation of tattoos and other related markings, various embodiments using chelated iron complexes can also be configured to minimize burning, erythema (e.g., redness) or other injury irritation of the skin resulting from the delivery of current to the skin for transdermal iontophoresis. This is due to several factors. First, minimizing the formation of precipitates prevents an increase in the skin's electrical impedance from such precipitates and in turn, the amount of ohmic heating of the skin. Further, when the ions stay in solution they increase the conductivity of the skin, thereby lowering impedance. Finally, because there is little or no precipitate, more of iontophoretically delivered iron is delivered to the subdermal tissue layers in a form which can be used by the body. Thus, the total time period of current delivery, and so the ampere hours, of delivered current is decreased, resulting in less damage to the skin. As discussed herein, it is desirable to keep the amount of total delivered current below a certain level for example below 100 mA-minutes, and still more preferably below 80 mA-minutes.

Various embodiments of the invention contemplate use of chelated complexes including chelated iron complexes on a wide variety of iontophoretic transdermal delivery platforms. These include embodiments employing DC current, AC current, single patch delivery, dual patch delivery, and multiple current embodiments including those employing one or more currents for producing oscillatory motion of the therapeutic agent as described in U.S. Provisional Patent Application Ser. No. 61/214,642, the contents of which are incorporated herein by reference (such embodiments involve the use of multiple AC currents delivered by separate pairs of electrodes which creates two electromotive forces acting on the iron or other active agent in its ionic form. The first force acts on the ions perpendicular to the skin surface, and driving them into the skin. The second force oscillates the ions horizontal to the surface of the skin producing a "sieving" action of the iron ions or other agent ions so as to funnel them through the stratum corneum, a process that is described as "oscillophoresis"). The electrical parameters (e.g., current, voltage, waveform, delivery time, etc.) as well as other parameters (e.g., patch size, agent solution concentration, etc.) can be adjusted for each platform to achieve a desired dosage of the selected therapeutic agent. Further, in various AC iontophoretic current embodiments, the current can be modulated (e.g., frequency, and/or amplitude modulation) to achieve one or more of the following: i) titrate the total delivered dose of therapeutic agent, ii) titrate (e.g., enhance) the rate of delivery of therapeutic agent (e.g., by increasing the current); iii) minimize the perceived pain of the patient (typically by keeping the amplitude below a specific level); and iv) minimize the amount of thermal injury and associated discoloration to the skin (e.g., by keeping the amplitude below a set level and/or the ampere-hours below a total amount). Modulation can be achieved using one or more embodiments of controller 150.

Use of chelated complexes is also contemplated for embodiments employing purely passive diffusion of therapeutic agent as well and combinations of passive and active diffusion (e.g., passive and iontophoretic transdermal delivery).

In various embodiments employing chelated iron complexes, such as iron pyrophosphate, the electrical parameters and delivery regimen can be configured to deliver therapeutically effective amounts of iron for treatment of iron deficiency anemia and related conditions. In various embodiments, the therapeutically effect amount of iron delivered using an iron chelated complex can be in the range from about 1 to about 300 mg, with specific embodiments of about 1 to about 100 mg, about 1 to about 50 mg, about 1 to about 25 mg and about 3 to about 10 mg. For embodiments employing ferric pyrophosphate, the amount of ferric pyrophosphate required to achieve these delivered doses is roughly three times the desired delivered dose, owing to the fact that iron makes up roughly one third of the molecular weight of ferric pyrophosphate. The concentrations of ferric pyrophosphate to achieve these dosages can be in the range of about 10 to 50 mg/ml with specific embodiments of 20, 30 and 40 mg/ml. So for example, for a patch holding about 1 ml of solution, the concentration of ferric pyrophosphate required to deliver 10 mg of iron would be about 30 mg/ml. Different concentrations can be used for different sized patches. Concentrations can also be adjusted using dose response curve methodology.

Figure 8A:
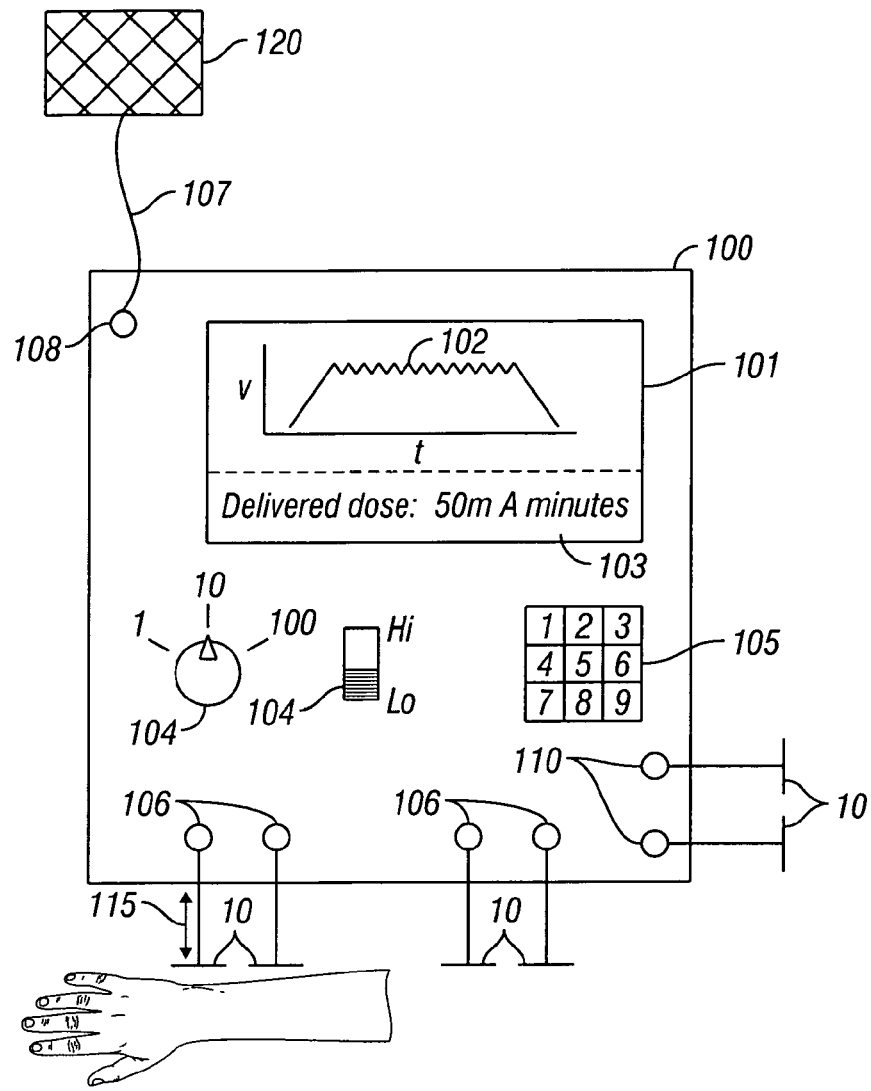
FIG. 8a is a schematic view illustrating an embodiment of a solar powered power supply.
Figure 8B:
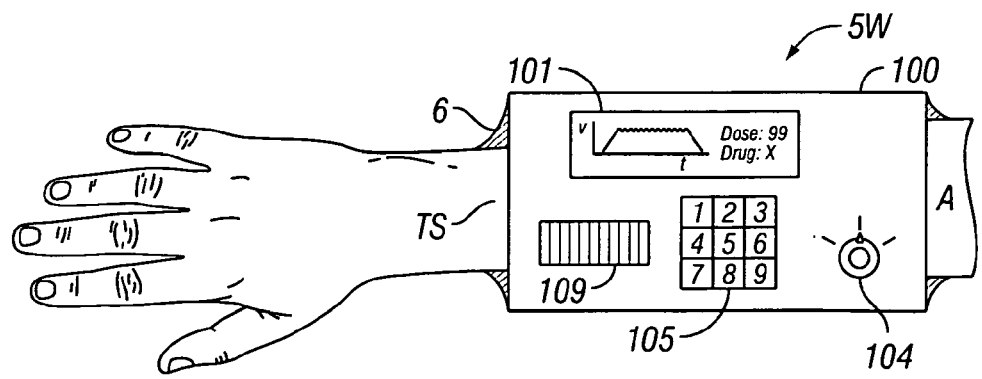
FIGS. 8b, 8c, 8d are top, cross sectional and perspective views illustrating embodiments of a wearable power supply.
Figure 8C:
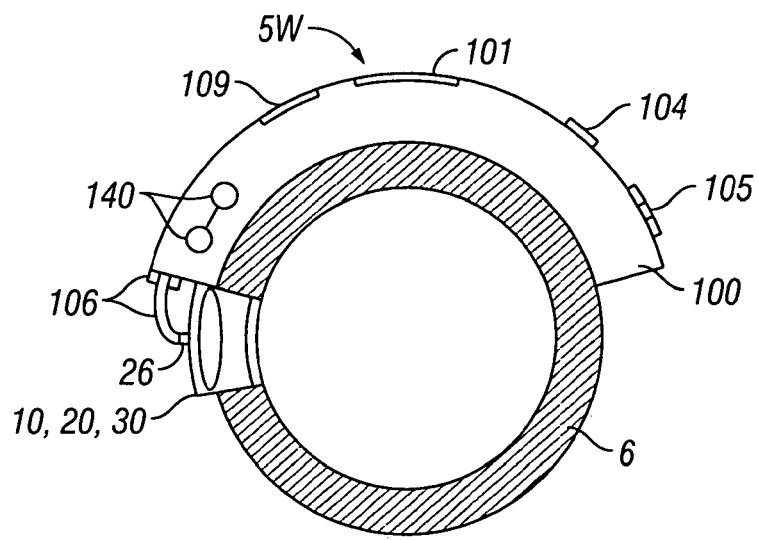
Figure 8D:
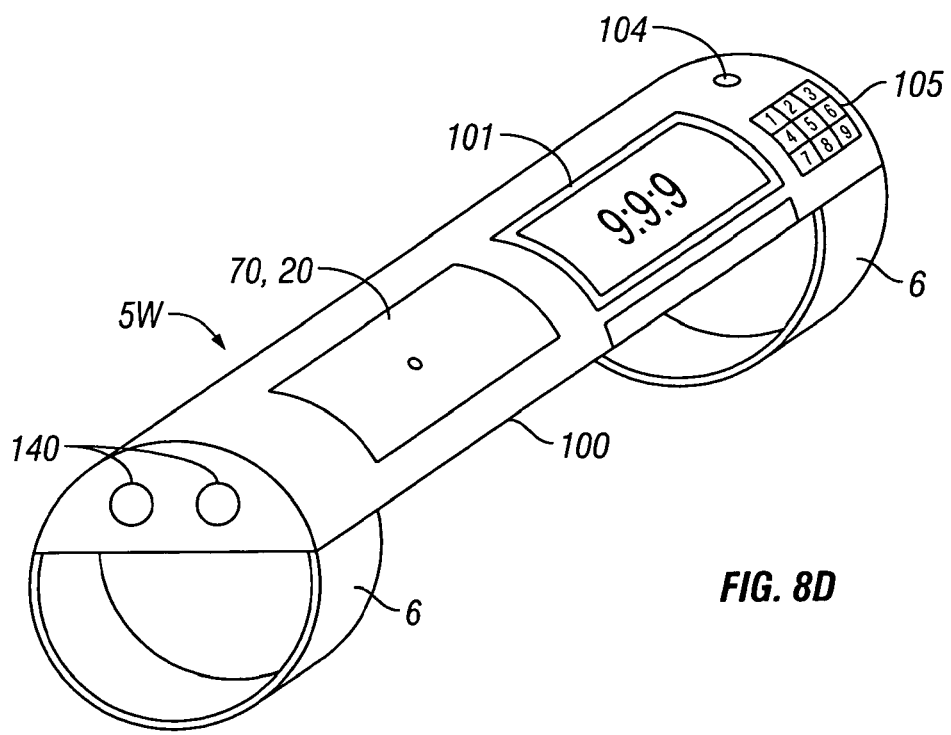
Figure 9:
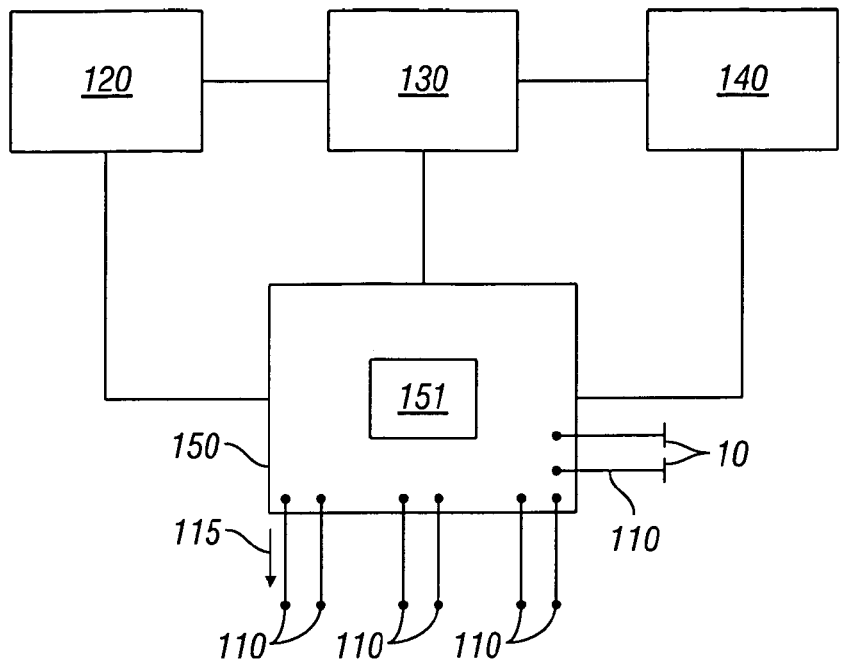
FIG. 9 is a block diagram illustrating the configuration of various components of an embodiment of the power supply.

Referring now to FIGS. 8-9, embodiments of power supply 100 will now be described. Various embodiments of the invention contemplate portable power supplies 100 that can be carried by hand and even worn by the user. In various embodiments, power supply 100 can be battery powered or may be powered by an external electrical power source (ac or dc). It may also be solar powered as is described herein.

An embodiment of a portable supply 100 shown in FIG. 8a, can include a display 101, for displaying electrical waveforms 102 and data 103, one or more control buttons/switches 104 for control and selection of various functions, touchpad/keys 105 for inputting data and one or more pairs of electrical connectors 106 for connecting to patch devices 10. The power supply can be battery powered or may also be powered by an external power AC or other power source. Also, in some embodiments the supply 100 can include a solar cell 120 as a direct power source and also to charge embodiments of supply 100 having rechargeable batteries discussed here. Solar cell 120 can be any number of photovoltaic cells and systems known in the art and has sufficient area and power generation characteristics to supply power to power supply 100 both for charging and direct power. In various embodiments, cells 120 can be configured to generate about 50 to 1000 watts of power with specific embodiments of 100, 200 and 500 watts. In specific embodiments, solar cell 120 can comprise silicon based cells including monocrystalline, polycrystalline and amorphous silicon. Additionally, cell 120 can be detachably coupled to supply 100 by means of cable 107 coupled to a power connector 108. Cable 107 can have sufficient length (e.g., 30 feet or longer) to allow the cell to be remotely placed in a window or roof or other location receiving direct or increased sunlight when supply 100 is being used in a location not receiving direct light.

In some embodiments, power supply 100 can be configured to have multiple output channels 110 so as to supply electrical/power signal 115 to multiple patch devices 10 and in turn allow for the transdermal iontophoretic delivery to multiple sites on a single patient or multiple patients. In preferred embodiments, the power supply can have up to eight channels 110, with additional numbers contemplated. Each channel 110 can be independently controlled through use of a controller 150 described herein, or other control means.

In many embodiments, power supply 100 can be a portable power supply 100 configured to be carried or even worn by the user, for example, on the arm of the user. In particular embodiments, the power supply 100 can be incorporated into a wearable system 5w (which includes patches 10) that is worn on the arm or leg or other location of a user. An embodiment of a wearable power supply 100 and system 5w is shown in FIGS. 8b, 8c and 8d. Wearable system 5w including power supply 100 can be configured to be to worn on the arm/leg of the user being attached to arm with an arm/leg band like device 6 or a similar device. It may also be configured to be attached to patch device 10 as described below. As another alternative, it may be worn on the user's belt and connected with connective wiring. For arm and leg wearable embodiments, wearable power supply 100 can have a curved or related form factor to facilitate wear on the arm or leg. It may even comprise conformable materials to conform to the shape of the arm or leg. Similar to portable supply 100, wearable supply 100 can also include a display 101, and one or more buttons or switches 104 as well as other features of embodiments of portable supply 100. It may also include a bar code reader 109 for reading bar codes on the packaging for kit 40, device 10 or container 30 as well as various other bar codes. It can also include one or more electrical connectors or fittings 106 for either directly engaging with connectors 26 of patches 10 or via cabling (not shown). The wearable power supply 100 can also be configured to attach arm band device 6 via VELCO or other attachment means (e.g., a snap or like fitting). Band device 6 can also be an integral component of power supply 100 allowing the user to easily slip or wrap band 6 around their arm or leg. As another alternative, embodiments of a wearable power supply 100 can be configured to directly attach to embodiments of patch 10 which include adhesive layers for attaching to the user's skin. Again, in such embodiments, power supply 100 can be attached to patch 10 via VELCRO or other attachments means.

Typically a wearable power supply will include a battery 140, though, power storage and/or generation means are also contemplated such as an energy harvesting device and/or a solar cell. Such alternative devices can be used alone or in conjunction with battery 140. Battery 140 can be lightweight and have a form factor to be readily integrated into the power supply. Suitable batteries can include alkaline, lead acid, nickel metal hydride, lithium, lithium ion cell, and like chemistries. The battery size can include double AA varieties known in the art. Other standard sizes are also contemplated.

In some preferred embodiments, power supply 100 can be configured to be solar powered and/or to have a battery rechargeable by solar power or other recharging means including a hand operated generator (such embodiments may also be configured for connection to an external power source). Accordingly, in these embodiments, power supply 100 will typically include a solar cell 120, recharging circuitry 130, a battery 140 and a controller 150 as is shown in the embodiment of FIG. 9. Suitable rechargeable batteries include lead acid, nickel metal hydride, lithium, lithium ion cell and like chemistries. The controller 150 will typically include a microprocessor 151 for controlling one or more functions of the power supply, memory resources for storing one or more software algorithms and data used by the microprocessor, a dc-dc converter for increasing voltage from the battery, a dc-ac converter for supplying AC power to one or more devices 10 and a multiplexor or power rail for supplying separate power/electrical signals 115 to each channel 110. The microprocessor can include one or more algorithms for controlling various functions of the power supply 100, for example the power regimen to device 10 for a particular therapeutic agent and particular patient.

Through use of controller 150, various embodiments of power supply 100 can be configured to perform multiple functions. These include i) generating and supplying voltage and current to one or more devices 10, ii) generating a specific power/electrical signal 115 for each device 10; iii) implementing power/signal regimens (e.g., current, voltage and frequency and waveforms over a duty cycle) for particular patients and therapeutic agents); iv) monitoring the voltage, current, impedance and current dose on each channel; v) regulating including modulating the signal (e.g., voltage, current and frequency) for each channel based on the monitored voltage, current, etc; and vi) perform various power management functions including detecting battery charge, charging the batteries and switching between battery and solar power when needed.

Various embodiments of power supply 100 can also be configured to supply selectable voltages and currents to one or more patch devices 10. In various embodiments, voltages can be in the range 1-14 volts with specific embodiments of 5, 6, 7, 8, 9, 10, 11, 12 or 13 volts. In specific embodiments the power supply can also be configured to have different voltage operating modes, for example, a low, medium and high voltage operating mode which can correspond to exemplary ranges of 1-6, 6-12, and 12-14 volts, with other ranges also contemplated.

Currents can be in the range of 0.1 to 0.8 ma, with specific embodiments of 0.1, 0.2, 0.3 and 0.4 ma, with other values contemplated. The controller can also include algorithms for limiting the total current dose (in amperes hours) delivered to the patient. In specific embodiments, the total current dose can be limited to below 100, 80, 60 or 40 mA-minutes. In various embodiments, the controller can shut off current when the maximum dose is reached or switch the polarity of the voltage so that therapeutic agent is now delivered from the other electrode assembly/patch (for dual patch embodiments). The controller can also be configured to decrease the current, e.g., from 0.3 ma to 0.1 ma, as the maximum current dose is approached. In this way the desired amount of therapeutic agent can be delivered without exceeding a current dose threshold.

In various embodiments, controller 130 can be configured to generate signals 115 having specific characteristics as well as a particular duty cycle of signals 115 depending upon one or more factors such as the therapeutic agent, patient and medical condition to be treated. The signal 115 can be DC, AC or a combination of both. For DC embodiments, signal 115 can have a range of 1 to 100 volts. In both DC and AC embodiments, signal 115 can be current controlled by controller 150 so that current is fixed and the voltage will vary. In these and related embodiments, the current can be controlled in the range from about 10 μa to 4 ma. Whether DC or AC, signal 115 can be modulated to perform one or more of the following functions including: i) minimization of pain perception by the patient (e.g., by amplitude modulation), ii) titration of the rate of delivery of the therapeutic agent; and iii) titration of the total amount of therapeutic agent delivered.

Figure 10A:
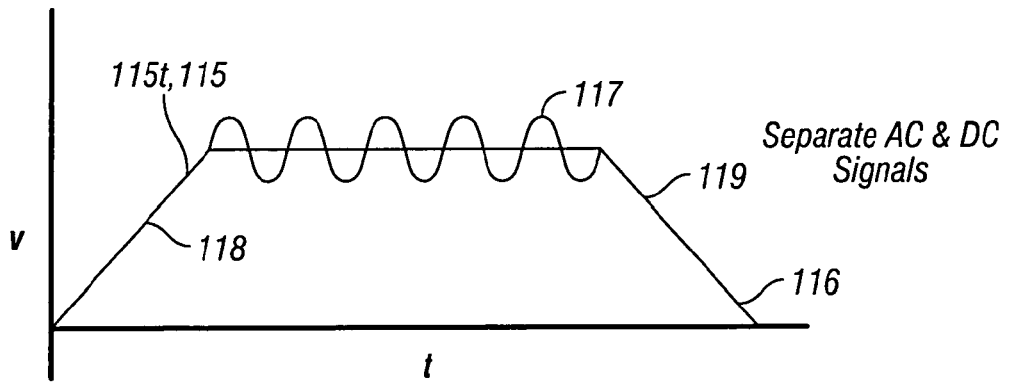
FIGS. 10a and 10b are plots showing embodiments of an electrical signal waveform having DC and AC components that is used for providing the electromotive force for transdermal iontophoretic delivery of a therapeutic agent.
Figure 10B:
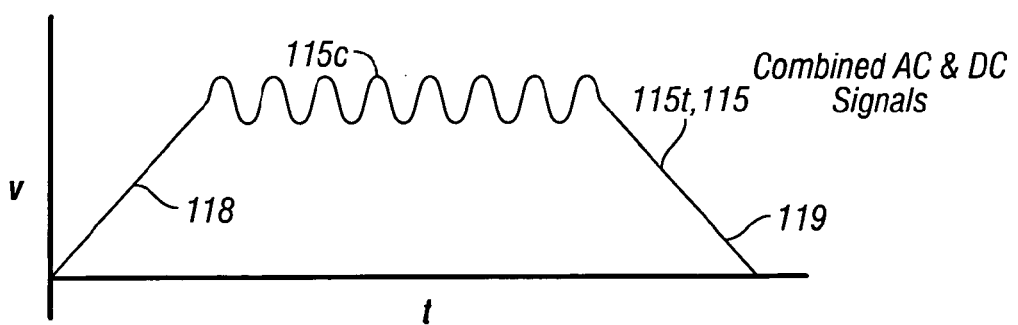
Figure 11:
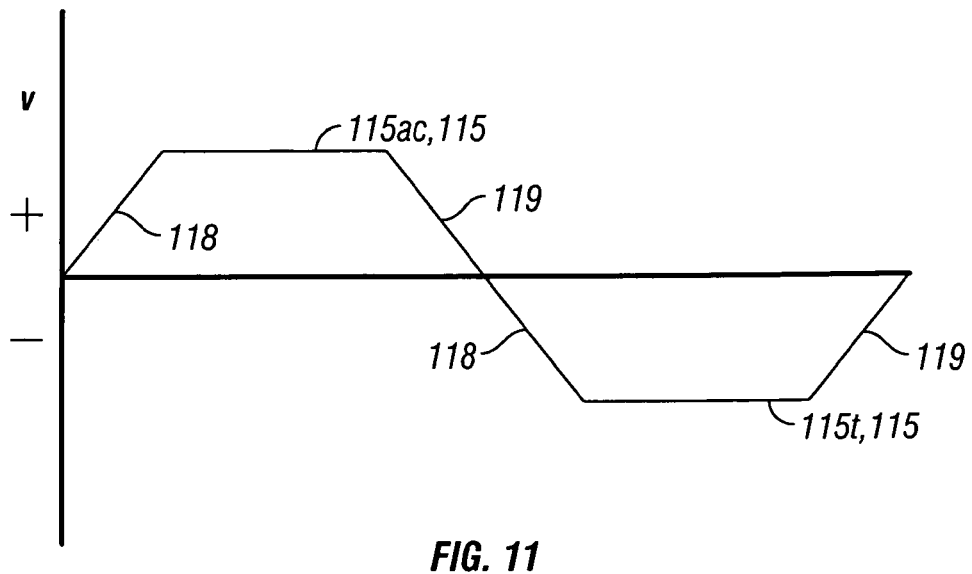
FIG. 11 is a plot showing an embodiment of an AC signal waveform used for providing the electromotive force for transdermal iontophoretic delivery of a therapeutic agent.

Referring now to FIGS. 10a, 10b and 11, in specific embodiments, signal 115 can comprise a combined signal 115c having a DC signal 116 component and an overlying AC signal component 117. AC component 117 can be configured to perform several functions including breaking down the capacitive charge buildup in skin tissue that can occur during application of a transdermal current or voltage as is shown in the embodiments of FIGS. 10a and 10b. It can also be configured to oscillate the chelated complex 55 in one or more directions with respect to the skin to enhance transport of the complex through the skin. The amplitude of signal 117 can be in the range of 1 to 100% of the DC signal with specific embodiments of 10, 20 and 50%. AC component 117 can be shaped to as to comprise a sine, square or saw-tooth wave, with a frequency in range between about 1 to 100 hz, about 1 to 50 hz, about 1 to 25 hz, and about 1 to 10 hz. Also, in these and other embodiments, signal 115 can have a trapezoidal 115t or other related shape wherein the voltage is slowly ramped up during ramp-up portion 118 and ramped down during a ramp-down portion 119. The slope of portions 118 and 119 are configured to decrease any pain felt by the patient as a result of a sudden increase or decrease in transdermally applied voltage.

Figure 12:
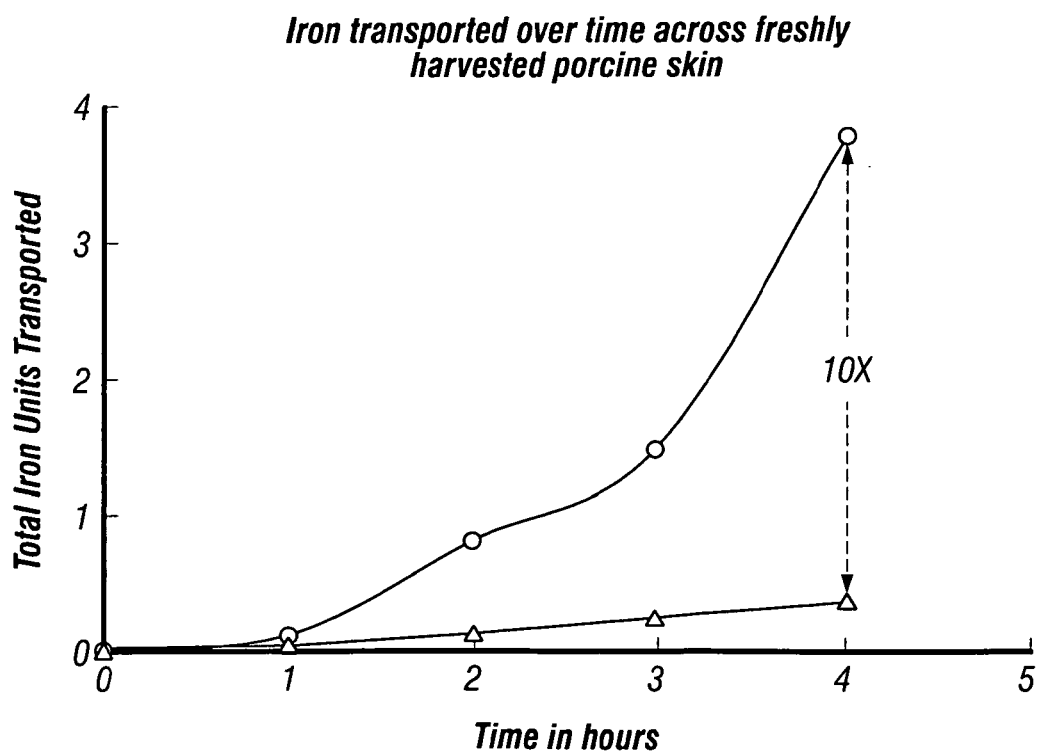
FIG. 12 is a plot illustrating the amount of ferrous chloride delivered across porcine skin using DC and AC waveform.

Also in many embodiments, signal 115 can substantially comprise an AC signal 115ac where the voltage is reversed in polarity at a set frequency as shown in the embodiment of FIG. 11. The frequency of the AC signal can be in the range from about 1 to 100 hz, about 1 to 50 hz, about 1 to 25 hz, and about 1 to 10 hz. The waveform of signal 115 can comprise a trapezoidal 115t or other like shape where voltage is ramped up and ramped down. Other waveforms are also contemplated including sine wave, etc. In use, such AC signal embodiments can significantly increase the amount of delivered therapeutic agent 51 by one or more means including preventing and/or breaking up the buildup of capacitive charge in the skin as well as the buildup of ionic layers in the skin, both of which can impede the transport of the therapeutic agent 51 into the skin that is driven by applied transdermal voltage. It can also do so by oscillating the therapeutic complex 55 in one or more directions with respect to the skin to find pathways of least resistance through the skin, such as through gaps in the stratum corneum. In one example shown in FIG. 12, nearly a 10 fold increase was obtained in the transport of ferrous chloride through porcine skin for the use of an AC vs. a DC signal.

In various embodiments, the power supply 100 can include various features to facilitate use by medical personnel both in a hospital setting and in the field. For example, the power supply can include or be configured to be coupled to a bar reader (not shown) for reading bar codes on the packaging for kit 40, device 10 or container 30 as well as various other bar codes. Additionally the power supply can include a clamp for attaching it the supply to an IV pole or other support stand or device.

Also in various embodiments, supply 100 including its electronic components can be configured to have enhanced durability and reliability so as to withstand various temperature and humidity extremes to allow its use in a variety of ambient conditions and environments, including tropical and desert environments. This can be achieved through the use of mil spec electronic components known in the art as well as the use of various protective polymer coverings and coatings internally and externally to confer resistance to moisture, sand and dust. Additionally, the power supply may constructed to have a high degree of fault tolerance and thus be constructed from fault tolerant components and/or have backup components such as a backup battery and a controller. Additional, backup components are also contemplated. Further one or more of the electronic components of the power supply can be configured to be modular to allow for rapid and easy replacement without having to replace the whole unit. This can be facilitated by the use of diagnostic software incorporated into controller 150 to identify faulty modules and components or when components are showing indications of failure or need for replacement. For example battery management software can indicate when the supply's battery, such as a lead acid battery, is approaching the end of its cycle life. This can be achieved by analyzing the voltage waveform of the battery under a load.

CONCLUSION

The foregoing description of various embodiments of the invention has been presented for purposes of illustration and description. It is not intended to limit the invention to the precise forms disclosed. Many modifications, variations and refinements will be apparent to practitioners skilled in the art. For example, the iontophoretic patch can be modified in size, shape and dose of therapeutic agent for different medical conditions, different tissue sites as well as for various pediatric applications. Also, embodiments of the invention have broad application for the treatment of a number of diseases and conditions which may benefit from transdermal delivery of a therapeutic agent and to do so in manner which reduces or prevents the likelihood of irritation or discoloration of the skin.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as stand-alone elements. Hence, the scope of the present invention is not limited to the specifics of the described embodiments, but is instead limited solely by the appended claims.

What is claimed is:

1. A method for the iontophoretic transdermal delivery of a chelated iron complex, the method comprising:
applying an iontophoretic transdermal delivery device to the skin of a subject, the device comprising an electrode and iron comprising a chelated iron complex comprising ferric pyrophosphate;
delivering an electrical current to the skin using the electrode; and
thus transporting the chelated iron complex across the skin, wherein the complex is transported across the skin without precipitation of iron in the skin, thereby reducing chromogenic reactions with the skin relative to the transport of non-chelated iron.

2. The method of claim 1, wherein the iontophoretic transdermal delivery device comprises a patch.

3. The method of claim 1, wherein the complex releases iron available for heme synthesis.

4. The method of claim 1, wherein the complex is transported without producing injury or irritation to the skin.

5. The method of claim 4, wherein the injury or irritation is erythema.

6. The method of claim 1, wherein the complex is transported without producing a cosmetic change to the skin.

7. The method of claim 6, wherein the cosmetic change is a tattoo.

8. The method of claim 1, wherein the iron complex is dissociated by phagocytosis.

9. The method of claim 1, wherein the iron is delivered to a sub-dermal tissue layer.

10. The method of claim 1, wherein the iontophoretic transdermal delivery device comprises a therapeutically effective amount of iron for the treatment of iron deficiency.

11. The method of claim 1, wherein the complex is transported without an increase in the electrical impedance in the skin from precipitation of iron in the skin.

12. The method of claim 1, wherein the complex is transported without a temperature increase in the skin from ohmic heating resulting from precipitation of iron in the skin.

13. The method of claim 1, wherein up to about 10 mg of elemental iron is transported across the skin.

14. The method of claim 1, wherein up to about 20 mg of elemental iron is transported across the skin.

15. The method of claim 1, wherein up to about 30 mg of elemental iron is transported across the skin.

16. The method of claim 1, wherein the current comprises an alternating current.

17. The method of claim 1, wherein the current has a waveform having a square wave, sine wave, saw tooth or trapezoidal shape.

18. The method of claim 1, wherein the current comprises an alternating current component and a direct current component.

19. The method of claim 1, wherein the current is modulated.

20. The method of claim 19, wherein the current is modulated in frequency.

21. The method of claim 19, wherein the current is modulated by a controller.

22. The method of claim 19, wherein the current is modulated to minimize pain perception.

23. The method of claim 19, wherein the current is modulated to minimize thermal injury to the skin.

24. The method of claim 19, wherein the current is modulated to reduce discoloration of the skin.

25. The method of claim 19, wherein the current is modulated to enhance transport of the chelated iron complex across the skin.

26. The method of claim 19, wherein the current is modulated to titrate delivery of the chelated iron complex across the skin.

27. A method for treating iron deficiency in a patient, the method comprising:
applying an iontophoretic transdermal delivery device to the skin of the patient, the device comprising an electrode and iron comprising a chelated iron complex comprising ferric pyrophosphate;
delivering an electrical current to the skin using the electrode;
thus transporting a therapeutically effective amount of the chelated iron complex across the skin, wherein the complex is transported across the skin without precipitation of iron in the skin, thereby reducing chromogenic reactions with the skin relative to the transport of non-chelated iron; and
dissociating the complex in tissue to release the iron, thus treating the iron deficiency.

28. The method of claim 27, wherein the complex is transported without an increase in the electrical impedance in the skin from precipitation of iron in the skin.

29. The method of claim 27, wherein the complex is transported without a temperature increase in the skin from ohmic heating from precipitation of iron in the skin.

30. A method for treating iron deficiency in a patient, the method comprising:
applying an iontophoretic transdermal delivery device to the skin of the patient, the device comprising an electrode and iron comprising a chelated iron complex comprising ferric pyrophosphate;
delivering an electrical current to the skin using the electrode;
thus transporting a therapeutically effective amount of the chelated iron complex across the skin, wherein the iron is sufficiently electrostatically bound by the chelating agent so that the iron is not available to form insoluble salts within the skin during transport, thereby reducing chromogenic reactions with the skin relative to the transport of non-chelated iron; and
dissociating the complex in tissue to release the iron, thus treating the iron deficiency.

31. The method of claim 30, wherein the dissociation of the complex releases iron available for heme synthesis.

32. The method of claim 30, further comprising: enhancing one of an amount of heme synthesis or blood hemoglobin utilizing the released iron.

33. The method of claim 30, wherein up to about 10 mg of elemental iron is transported across the skin.

34. The method of claim 30, wherein up to about 20 mg of elemental iron is transported across the skin.

35. The method of claim 30, wherein up to about 30 mg of elemental iron is transported across the skin.

36. The method of claim 30, further comprising: titrating the transport of the chelated iron complex in response to a biomarker of iron status.

37. The method of claim 36, wherein the biomarker of iron status is a serum concentration of iron, ferritin or a transferrin iron saturation.

38. The method of claim 36, wherein the transport rate or total amount of chelated iron complex transported is titrated.

* * * * *